United States Patent [19]

Wu et al.

[11] 4,204,839
[45] May 27, 1980

[54] FLUORIMETRIC ANALYSIS METHOD FOR BILIRUBIN

[75] Inventors: Tai-Wing Wu, Rochester; Sheryl S. Sullivan, Hilton, both of N.Y.

[73] Assignee: Eastman Kodak Company, Rochester, N.Y.

[21] Appl. No.: 932,158

[22] Filed: Aug. 9, 1978

[51] Int. Cl.$^2$ ............................................. G01N 33/16
[52] U.S. Cl. ..................................... 23/230 B; 23/905
[58] Field of Search .............................. 23/230 B, 905

[56] References Cited

U.S. PATENT DOCUMENTS

| | | | |
|---|---|---|---|
| 4,069,016 | 1/1978 | Wu | 23/230 B |
| 4,069,017 | 1/1978 | Wu | 23/230 B |

OTHER PUBLICATIONS

J. Kresner, Biochemical Medicine, vol. 7, pp. 135–144 (1973).

A. Cu et al., Journal of the American Chemical Soc., vol. 9719, pp. 2579–2580 (1975).

T. Vete, Clin. Chim. Acta, 59(2), 259–261 (1975).

*Primary Examiner*—Sidney Marantz
*Attorney, Agent, or Firm*—Ronald P. Hilst

[57] ABSTRACT

Fluorimetric analysis of bilirubin contained in an aqueous liquid is carried out by the method comprising:
(a) contacting together the aqueous liquid and an interactive, polymeric mordant composition for bilirubin to mordant bilirubin;
(b) thereafter, or during step (a), subjecting the mordanted bilirubin to activating radiation effective to excite the mordanted bilirubin and produce detectable fluorescence; and
(c) detecting this fluorescence to obtain a determination relating to the presence and/or concentration of bilirubin in the test sample.

20 Claims, 1 Drawing Figure

FLUORIMETRIC ANALYSIS METHOD FOR BILIRUBIN

Field of the Invention

The present invention relates to a fluorimetric method for analysis of bilirubin in various liquid samples, particularly biological liquids including body fluids such as blood, serum, urine and the like.

The method is direct and can provide a quantitative determination of bilirubin. The method may employ "wet" or "dry" chemistry. "Wet chemistry" refers to analytical chemical techniques, sometimes termed solution assay techniques, wherein chemical reagents are dissolved or suspended in a liquid vehicle. "Dry chemistry" refers to analytical chemical techniques wherein chemical reagents are present in various substantially "dry-to-the-touch" elements such as "dip-and-read" test strips, multilayer analytical test elements, and the like.

BACKGROUND OF THE INVENTION

Bilirubin is a degradation product of hemoglobin. According to estimates, approximately 6 to 7 grams of hemoglobin are released from damaged or aged red blood cells each day. The liver, spleen, and bone marrow rapidly degrade this pool of hemoglobin resulting in approximately 200 to 230 milligrams of bilirubin and its derivatives being formed each day in the normal human adult. Subsequently, as a part of normal human metabolic processes the major portion of this daily bilirubin production is excreted, degraded into other derivatives, etc.

In some cases, however, an excessive amount of bilirubin occurs within the human body through overproduction of bilirubin, as in the case of excessive hemolysis, or by retention of bilirubin due, for example, to a liver failure. Invariably, jaundice results. This widely encompassing pathological condition is characterized by markedly elevated serum bilirubin levels, for example, 10 milligrams of bilirubin per deciliter of serum or higher compared to the normal adult range of 0.1 to about 1 milligram of bilirubin per deciliter of serum. There is generally also present a brownish-yellow pigmentation of the skin, sclera, or mucous membranes.

In addition, increasing evidence suggests that excess amounts of bilirubin in the blood can lead to an undesirable increase in bilirubin concentration within body cells and interfere with various cellular processes. For example, bilirubin has been widely implicated as a potent inhibitor of many enzymatic reactions that generate energy vital to the cell. Given this background, the clinical diagnostic significance of bilirubin in tests for liver and other related organ functions is self-evident.

Perhaps the most widely used analytical procedure for bilirubin assay work has been the so-called diazo method. The diazo method employs a coupling reaction of bilirubin with a diazonium salt, such as diazosulfanilic acid, to form a pigment having an extinction coefficient higher than bilirubin by itself (which has a yellowish coloration). The diazo method, however, has a variety of problems. For example, as noted in *Clinical Chemistry-Principles and Technics*, edited by R. J. Henry, D. C. Cannon, and J. W. Winkelman, Harper and Row Publishers, 2nd Edition, pages 1042–1079 (1974), because of the many variants and the complexity of the diazo method, the determination of bilirubin for a given sample is often quite different for different variants of the diazo method. In addition, the diazo method can be time-consuming because it typically requires several reagents which generally are freshly mixed for each determination. Moreover, the diazo method can be inaccurate because certain body fluid components other than bilirubin respond to diazotization.

Wu et al, U.S. Pat. No. 4,069,017 issued Jan. 17, 1978, describes a new assay for the determination of bilirubin. This patent discloses that certain interactive mordant compositions can be effectively employed to mordant bilirubin. Such mordanted bilirubin greatly facilitates the colorimetric detection of bilirubin in an aqueous liquid sample. The mordanted bilirubin exhibits a marked increase in molar extinction coefficient and a shift in absorption peak in comparison to that of free bilirubin.

The assay method of U.S. Pat. No. 4,069,017 is colorimetric, and there is no disclosure of modifying this method to provide a fluorimetric assay. Such modifications would be highly advantageous for at least several reasons. First, as is well-known, fluorimetric assays are capable of greater sensitivity than is possible with colorimetric assays. Second, although the assay method described in U.S. Pat. No. 4,069,017 is colorimetric, it has many advantages which would also be useful in a fluorimetric assay. For example, the assay method of U.S. Pat. No. 4,069,017 is direct, quantitative, substantially free of interferents, and can be performed with ease.

Based on the foregoing reasons, any adaptations or modifications of the colorimetric bilirubin assay described in U.S. Pat. No. 4,069,017 to provide a fluorimetric bilirubin assay would clearly represent an extremely valuable contribution to the art.

SUMMARY OF THE INVENTION

The present invention provides a fluorimetric method for the analysis of bilirubin in an aqueous liquid wherein an interactive, polymeric mordant composition for bilirubin is contacted together with the aqueous liquid to mordant bilirubin. The method comprises the novel step of subjecting the mordanted bilirubin to activating radiation effective to excite the mordanted bilirubin and product detectable fluorescence indicative of the presence or concentration of bilirubin in the liquid.

More specifically, the method comprises the following steps:
(a) contacting together the aqueous liquid with an interactive polymeric mordant composition for bilirubin to mordant bilirubin;
(b) thereafter, or during step (a), subjecting the mordanted bilirubin to activating radiation effective to excite the mordanted bilirubin and produce detectable fluorescence; and
(c) detecting such fluorescence to provide a determination relating to the presence and/or concentration of bilirubin contained in the aqueous liquid.

In one preferred embodiment, the mordanted bilirubin is excited with activating radiation containing radiation having a wavelength within the range of about 420 to 475 nm to produce detectable fluorescence which is detected in a wavelength range of from about 480 to 525 nm.

This fluorimetric method of bilirubin determination provides a number of highly useful advantages. Not only does the method provide an increase in sensitivity because it is fluorimetric, but also the method employs certain of the same interactive mordant compositions for bilirubin as described in U.S. Pat. No. 4,069,017.

These interactive mordant compositions are known to provide a highly useful colorimetric determination for bilirubin. Thus the present invention provides the opportunity to employ as an interactive composition for bilirubin an interactive mordant composition that produces colorimetrically and fluorimetrically detectable changes, either or both of these changes representing a highly useful qualitative or quantitative bilirubin determination. Moreover, the method of the invention can be conveniently carried out using either "dry chemistry," or "wet chemistry" analytical techniques.

In addition, the fluorimetric method of the invention provides the opportunity of achieving an unusually high degree of bilirubin sensitivity because of the extremely high fluorescence intensity exhibited by bilirubin when mordanted by certain of the preferred interactive mordant compositions described herein. More specifically, as shown hereinafter in Example 6, the fluorescence intensity of the preferred bilirubin-mordant complexes employed in the method of the present invention is markedly higher than the fluorescent intensity exhibited by bilirubin in the presence of certain other materials which are known to cause bilirubin to fluoresce, such as albumin as described by J. Kresner, *Biochemical Medicine*, Vol. 7, p. 135–144 (1973) or the detergent cetyltrimethyl ammonium bromide as described by A. Cu et al, *Journal of the American Chemical Society*, Vol. 9719, p. 2579–2580 (1975). Thus, the fluorimetric analysis method of the invention provides a degree of bilirubin sensitivity beyond that achieved by many conventional techniques for inducing bilirubin fluorescence.

The interactive mordant compositions employed in the present method include certain of those described in U.S. Pat. No. 4,069,017. The mordant compositions of interest in the present method are polymers having binding sites for bilirubin, such polymers comprising repeating units having a hydrophobic matrix and at least one charge-bearing cationic group. Bilirubin interacts with these polymeric mordant compositions and, as a result, bilirubin is mordanted, i.e., binds to the mordant composition.

In a preferred embodiment, the bilirubin analysis method is carried out with a "dry chemistry" analytical element as follows:

(a) contacting together the aqueous liquid and an analytical element having an essentially dry reagent zone comprising an interactive, polymeric mordant composition, as described above, to produce mordanted bilirubin in the element;

(b) subjecting the element containing such mordanted bilirubin to activating radiation effective to excite the mordanted bilirubin and produce detectable fluorescence; and (c) detecting such fluorescence.

In accord with an especially preferred embodiment, the dry chemistry analytical element employed in the method of the invention is a multi-zone element comprising a reagent zone as described above and a spreading zone which can effectively distribute and meter the aqueous test sample to the reagent zone. Typically, in this embodiment, such multi-zone elements are integral elements wherein the spreading zone and reagent zone are superposed layers in fluid contact with one another under conditions of use of the element. Optionally, these layers can be carried on a suitable support, such as a "radiation transmissive" support.

The term "radiation-transmissive" refers to zones, supports, and other layers of an element that permit effective passage of electromagnetic radiation used to excite and detect a fluorescent analytical result produced in the element in accord with the invention. Typically, such "radiation-transmissive" zones, supports, and other layers are transmissive of radiation having a wavelength within the region of from about 200 to about 800 nm.

DESCRIPTION OF THE PREFERRED EMBODIMENT

Figure 1:
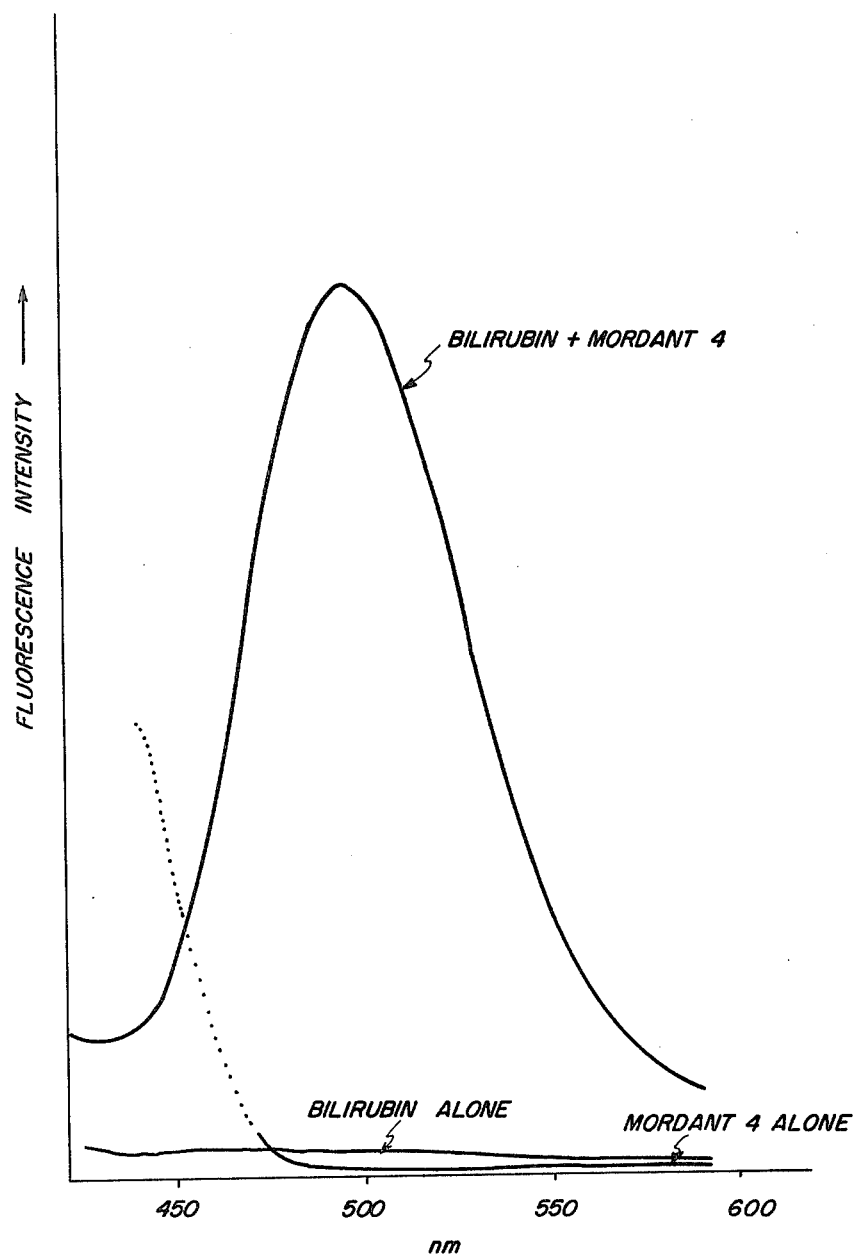
FIG. 1 is a graph showing typical fluorescence spectra of bilirubin, a preferred polymeric mordant for bilirubin, and bilirubin bound to this mordant.

The present invention provides a method for the analysis of bilirubin in an aqueous liquid test sample by contacting together the test sample with the aforementioned interactive mordant composition for bilirubin. Although the pH and temperature conditions under which this contacting step is carried out can vary considerably, in certain preferred embodiments this contacting step is carried out at a pH range of from about 6.8 to about 9.5, preferably about 6.8 to about 7.6, and at a temperature within the range of from about 15° to about 60° C., preferably from about 22° to about 50° C. Of course, depending upon the particular interactive mordant composition selected, one can vary the aforementioned pH and temperature to values above or below the stated ranges, providing, of course, that one does not use a pH or temperature which causes undesired side reactions or significant degradation of bilirubin or the interactive mordant composition.

To aid in maintaining the pH within the stated range of from about 6.8 to about 9.5, the bilirubin determination is typically carried out in the presence of buffer. Various buffers can be used such as those described by Good in *Biochemistry*, 5, 467 (1966). Particularly good results have been obtained using phosphate buffers, such as sodium phosphate, in an amount effective to maintain the pH of the aqueous test sample in the presence of the interactive mordant composition within the range of from about 6.8 to about 7.6.

During or following the above-described contacting step in which bilirubin interacts with the mordant composition to produce mordanted bilirubin, the mordanted bilirubin is subjected to activating radiation effective to excite and produce the fluorescence characteristics of the mordanted bilirubin. Activating radiation effective to produce such fluorescence can vary depending upon the particular interactive mordant compositions selected for use. In accord with certain preferred embodiments, radiation having a wavelength of about 420–475 nm has been found effective to produce fluorescence emission of the mordanted bilirubin occurring at a wavelength within the range of from about 480 to 520 nm. In general, useful activating radiation effective to excite the mordanted bilirubin is radiation corresponding to a characteristic absorption maxima of bilirubin, preferably the absorption maximum of bilirubin which occurs at about 435 to 440 nm. The peak wavelength of the corresponding fluorescence emission may, of course, vary somewhat from the 480 to 520 nanometer range noted hereinabove, depending upon the particular interactive mordant composition for bilirubin which is selected.

The fluorescence emission characteristic of the interaction product formed by bilirubin and the mordant compositions described herein appears to be formed solely by this interaction product. Neither bilirubin alone, nor the interactive mordant composition alone exhibits fluorescence emission in the 480 to 520 nm range when subjected to activating radiation. Moreover, as shown in the appended examples, the intensity of the characteristic fluorescence emission obtained by the interaction product of bilirubin and these mordant compositions has been found to increase as the amount of bilirubin contained in a given aqueous test sample increases. Thus, the fluorimetric bilirubin determination method of the invention provides not only a qualitative, but a quantitative method for the determination of bilirubin.

The interactive mordant compositions employed in the method of the invention include certain of the mordant compositions for bilirubin described in the aforementioned U.S. Pat. No. 4,069,017. In general, these mordant compositions are polymers having bilirubin binding sites, and these polymers contain repeating units which comprise a hydrophobic, organic matrix and at least one charge-bearing cationic group. Such mordants can be homopolymers or copolymers containing repeating units having the above-defined properties. Materials having these properties and composition, upon interaction with bilirubin, have been found to produce the characteristic fluorescence emission providing the basis for the bilirubin determination method of the invention.

Especially preferred polymeric interactive mordant compositions are materials having in the polymeric chain, monomer units of formula I below:

I.

wherein

A represents an organo group and constitutes a portion of a polymer backbone;

Q represents a chemical bond(s) or a chemical group linking M⊕ to A;

M⊕ represents a cationic group, preferably a quaternary ammonium or phosphonium group; and X⊖ represents an acid anion such as a halide ion, for example, chloride or bromide; nitrate; methosulfate; p-toluenesulfonate; or an equivalent anion.

In certain especially useful embodiments, M⊖ represents a quaternary ammonium or phosphonium group having Formulas II or III below:

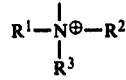

II.

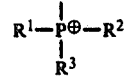

III.

wherein each of $R^1$, $R^2$, and $R^3$, which may be the same or different, represent an aryl, an aralkyl, or an alkaryl group having from about 5 to 20 carbon atoms or an alkyl group having from 1 to about 10 carbon atoms, preferably 4 to about 10 carbon atoms.

Preferably, Q, in Formula I represents a hydrocarbon group, preferably an arylene, arylenealkylene, alkylenearylene, arylenebisalkylene, or alkylenebisarylene group. Typically, although not required, Q contains from about 5 to 10 carbon atoms.

As will be appreciated, A in Formula I above can vary depending upon the particular polymeric backbone selected for use. Especially good results, however, have been obtained when A represents an alkylene group. Typically, such alkylene groups contain from about 2 to 10 carbon atoms.

Copolymers particularly useful as interactive mordant compositions include copolymers containing recurring units having formula I hereinabove and, in addition, up to about 75 weight percent of additional repeating units comprising the residue of non-interfering monomers. The term "non-interfering repeating units" is used herein to include chemical units which do not chemically or physically interfere with the above-described mordanting of bilirubin. Monomer precursors which provide such non-interfering repeating units and which also impart hydrophobicity to the resultant mordant copolymer include aliphatic and aromatic hydrocarbons, such as olefins, substituted olefins, styrene, and substituted styrenes; alkylacrylates and methacrylates and derivatives thereof; and known equivalents for such monomer precursors. In addition, if desired, difunctional crosslinking groups can be introduced into such copolymers to provide crosslinked copolymers useful as interactive mordant compositions within the scope of the present invention.

A partial listing of individual representative interactive mordant compositions useful in the method of the invention include the following materials:

Table I

| Name | Structure |
|---|---|
| 1. Poly(N,N,N-trimethyl-N-vinyl-benzylammonium chloride) | 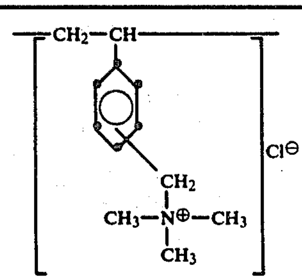 |

Table I-continued

| Name | Structure |
|---|---|
| 2. Poly[styrene-co-benzyl-(dimethyl)-p-vinyl-benzyl-ammonium chloride] | —[CH₂—CH(C₆H₅)]— [CH₂CH(C₆H₄)—CH₂—N⁺(CH₃)₂—CH₂—C₆H₅ Cl⁻] |
| 3. Poly(N,N,N-trioctyl-N-vinyl-benzylphosphonium chloride) | —[CH₂—CH(C₆H₄)—CH₂—P⁺(C₈H₁₇)₃ Cl⁻]— |
| 4. Poly[styrene -co-(vinylbenzyl)-(trihexyl)-ammonium chloride] | —[CH₂—CH(C₆H₅)]— [CH₂—CH(C₆H₄)—CH₂—N⁺(C₆H₁₃)₃ Cl⁻] |
| 5. Poly(N,N,N-trimethyl-N-vinylbenzylammonium chloride-co-styrene) | —[CH₂—CH(C₆H₅)]— [CH₂—CH(C₆H₄)—CH₂—N⁺(CH₃)₃ Cl⁻] |
| 6. Poly(styrene-co-N-vinyl-benzyl-N-benzyl-N,N-dimethyl-ammonium chloride-co-divinyl-benzene) | —[CH₂—CH(C₆H₅)]— [CH₂—CH(C₆H₄)—CH₂—N⁺(CH₃)₂—CH₂—C₆H₅ Cl⁻] —[CH₂—CH(C₆H₄)—CH=CH₂]— |

Further extended description of such interactive mordant compositions including methods of preparing such compositions can be found by reference to U.S. Pat. No. 4,069,017 hereby incorporated by reference.

The amount of the above-described interactive mordant composition for bilirubin which is required in this method of bilirubin analysis can vary. Typically, in any given case, the amount of such interactive mordant composition will depend upon the particular range of bilirubin content, i.e., the "dynamic range", over which a specific bilirubin assay is designed to be useful. In accord with various preferred embodiments wherein 1 mole of bilirubin is bound or mordanted to an interactive mordant containing 1 molar equivalent amount of binding site for bilirubin, there should be sufficient interactive mordant to provide at least one molar equivalent of binding site for the maximum number of moles of bilirubin for which that assay is intended.

The amount of the interactive, polymeric mordant composition required will depend upon the average number of repeating units in the polymer containing a binding site for bilirubin and, as noted above, the dynamic range over which a specific bilirubin assay which employs such polymeric material is designed to be useful. In a preferred embodiment wherein a polymeric mordant, such as any one of polymeric mordants 1–6 listed above, is employed and wherein such polymeric mordant is prepared from an intermediate copolymer of styrene and vinylbenzyl chloride having an inherent viscosity (as measured at 25° C. in benzene at a concentration of 0.25 g/dl.) of about 0.15 to 1.0, one typically employs an amount of polymeric mordant within the range of from about 0.01 to about 1.0 g/dl. of mordant to provide an assay having a dynamic range of about 0.1 to 50 mg/dl. of bilirubin analyte.

In general, it is useful to employ an excess amount of interactive mordant composition in the bilirubin analysis method so that one can accelerate the interaction of bilirubin with the mordant to obtain the desired change in spectral properties of the mordanted bilirubin.

Wet-Chemistry Bilirubin Determination

When the bilirubin analysis method is carried out as a wet chemistry or solution assay, analysis is conveniently performed by preparing in a suitable "wet" reaction zone, such as a radiation-transmissive container, an appropriate interactive mordant composition dissolved or dispersed in a non-interfering liquid medium. Such non-interfering liquids include those liquids which, under conditions of use, do not substantially interfere with the interaction of bilirubin and mordant composition or provide unwanted fluorescence emission at the characteristic fluorescence emission peak of the mordanted bilirubin. Such non-interfering liquids include a variety of both aqueous and organic liquids. Typically, because of the application of the method to the analysis of biological fluids, the use of an aqueous liquid as the non-interfering liquid is preferred. If desired, and in a preferred embodiment, the reaction zone includes one or more buffers as described hereinabove to facilitate the performance of the assay in the preferred pH range of from about 6.8 to about 9.5.

When the analysis method is carried out as a "wet" assay for bilirubin, a preliminary step of treating the bilirubin-containing liquid test sample to dissociate the bilirubin from various materials to which it may be bound is quite desirable. For example, where the liquid test sample is serum, a large amount of the bilirubin is bound to serum protein, primarily albumin. Various techniques have been devised in the art and are well-known to dissociate bilirubin from materials such as albumin, and such methods may be employed as the preliminary treatment step so that the resultant assay provides an accurate determination of total bilirubin contained in the serum sample. These methods include the use of various protein precipitation techniques, sample dilution techniques, and the like. A review of many of these different procedures can be found, for example, in the aforementioned Winkelman et al publication, i.e., *Clinical Chemistry-Principles and Technics,* 2nd Edition (1974), pages 1042–1079.

Following the preparation of an appropriate interactive mordant composition in a non-interfering liquid in a wet reaction zone, as well as any optional preliminary treatment of the bilirubin-containing test sample as described above, the bilirubin analysis method can be carried out by contacting together the liquid test sample with the interactive composition contained in the non-interfering liquid. If desired, this can be carried out in the dark or under yellow safelight conditions to avoid light induced degradation of bilirubin. Typically, the non-interfering liquid containing the interactive mordant composition is incubated with liquid test sample for a suitable period to effect interaction of the bilirubin in the test sample and the interactive mordant composition. Thereafter, or during this step, the wet reaction zone containing the mixture of liquid test sample and interactive composition can then be subjected to suitable activating radiation to produce the characteristic fluorescence emission.

Where an incubation period is employed, the time is typically quite short, on the order of seconds or minutes, typically within the range of from about one second to about 10 minutes, preferably 30 seconds to about 4 minutes. If desired, stirring or mixing of the assay reaction mixture can be carried out during the incubation period to facilitate interaction of the bilirubin and interactive mordant composition. The temperature range maintained during the contacting and optional incubation period, as well as the subsequent subjection to activating radiation and fluorescence determination steps, are as stated hereinabove.

"Dry-Chemistry" Bilirubin Determination

Because of handling ease and overall convenience features as well as the capability of providing quantitative analytical results, the fluorimetric analysis of bilirubin in accord with the present invention by use of a "dry chemistry" analytical element is especially preferred. Such an element comprises an essentially dry (i.e., dry-to-the-touch) reagent zone containing the above-described interactive mordant composition. An essentially dry spreading zone and/or additional zones can also be present in the analytical elements. A preferred element of the invention typically comprises at least two distinct zones which are in "fluid contact" with one another under conditions of use. Fluid contact has reference to the ability of a liquid to pass between distinct zones of an element, even though the zones may be separated by intervening zones or initially spaced apart. Other zones which can be present in the element, if desired, include radiation-blocking zones, subbing zones, and the like.

Further description of radiation-blocking zones and the term "fluid contact" can be found in U.S. Pat. No. 4,069,017. Further description of subbing zones or layers and certain other optional zones or layers can be found in the following description of a preferred embodiment of a multi-zone element.

Preferably, although not necessarily, the various zones are present in an element as superposed, contiguous layers. Typically these layers are carried on a support, preferably a radiation transmissive support. Although preferred analytical elements of the invention are composed of superposed, contiguous layers, other elements can be prepared and employed in the method of the invention having different structural arrangements such as the use of an element having two adjacent abutting zones, namely a spreading zone and a reagent zone, both carried on a support, if necessary or desired. Such an element is illustrated, for example, in FIG. 2 of the aforementioned U.S. Pat. No. 4,069,017. For purposes of convenience and for illustrating the best mode of the invention, the dry chemistry elements employed in the invention will hereinafter be described in terms of their structure and characteristics as observed in a multilayer, integral analytical element wherein the different zones are present as superposed, contiguous layers carried on a radiation-transmissive support.

In one preferred embodiment, an integral analytical element of this invention comprises a radiation-transmissive support having thereon, (1) a reagent layer that is permeable to at least bilirubin and which contains an interactive mordant composition for bilirubin as described above, and (2) a spreading layer that is permeable to bilirubin. The reagent layer is interposed between the support and the spreading layer. Also, the spreading layer is preferably of substantially uniform permeability to bilirubin. Preferably, the reagent layer is substantially impermeable to protein materials having a molecular weight substantially greater than that of bilirubin, e.g., albumin and other protein materials having a molecular weight in the region of 60,000 (dalton units) or higher.

In accordance with a further aspect of the foregoing preferred embodiment, the spreading layer is a non-fibrous spreading layer, desirably isotropically porous. More preferably, all layers in the element are non-fibrous, to enhance quantitative analytical capability of the element. The term "non-fibrous" is used herein with respect to layers and/or materials to indicate that such layers or materials are free or substantially free from fibrous materials, that is, they do not include fibrous components to a degree that would interfere with sample spreading or with detection of the analytical result by radiometric means.

Useful spreading layers can be prepared using a variety of both fibrous and non-fibrous components. Especially preferred spreading layers containing non-fibrous components are more fully described in U.S. Pat. No. 3,992,158, issued Nov. 16, 1976. In one aspect such non-fibrous spreading layers are prepared from particulate material, all desirably chemically inert to sample components under analysis. Particulate materials such as pigments, diatomaceous earth, microcrystalline colloidal materials derived from natural or synthetic polymers, e.g., microcrystalline cellulose, glass or resinous beads, and the like, can advantageously be employed in such particulate spreading layers as described in U.S. Pat. No. 3,992,158. As an alternative or an addition to such particulate material, these preferred non-fibrous spreading layer compositions can be prepared using porous polymer compositions such as "blush" polymer compositions, as also described in detail in U.S. Pat. No. 3,992,158.

The thickness of the spreading layer is variable and will depend in part on the intended sample volume, which for convenience and cleanliness the spreading layer should to able to absorb, and on the void volume of the layer, which also affects the amount of sample that can be absorbed into the layer. Spreading layers of from about 50 microns to about 300 microns dry thickness have been found particularly useful. However, wider variations and thickness are acceptable and may be desirable for particular elements.

Reagent layers employed in the dry chemistry elements of the invention can include, if desired, a matrix in which the interactive, polymeric mordant composition is distributed, i.e., dissolved or dispersed. However, because the interactive mordant composition is polymeric and may itself be film-forming or otherwise readily coatable as a uniform layer or zone, such an additional matrix material is not required. The choice of a matrix material is, of course, variable and dependent on the components of the interactive mordant composition distributed therein. In any case, the matrix material should be "non-interfering" with respect to the mordant composition, i.e., the matrix material should be incapable of itself binding or mordanting to the interactive mordant composition.

Desirable matrix materials for reagent layers associated with spreading layers are non-fibrous and can include non-interfering hydrophilic materials including acid hydrolyzed gelatins (e.g., pig gel) and derivatives thereof having an isoelectric point of about 9.1, hydrophilic cellulose derivatives, polysaccharides such as dextran, gum arabic, agarose and the like, and also synthetic substances such as water-soluble polyvinyl compounds like poly(vinyl alcohol) and poly(vinyl pyrrolidone), acrylamide polymers, etc. Non-interfering organophilic materials such as cellulose esters and the like can also be useful.

To enhance permeability of the reagent layer, it is often useful to use a matrix material that is swellable in the solvent or dispersion medium of liquid under analysis. Also, it may be necessary to select a material that is compatible with the application of an adjacent layer, such as by coating means, during manufacture of the element. As an example, where the formation of discrete contiguous layers is desired and the intended analysis will be of aqueous liquids, it may be appropriate to select an essentially water soluble matrix for the reagent layer and essentially organo-soluble or organo-dispersible ingredients for an adjacent layer, such as a spreading layer. In such manner, mutual solvent action is minimized and a clearly delineated layer structure can be formed. In many cases, to prevent diffusion of high molecular weight protein materials into the reagent layer (which materials may be potential bilirubin interferents), it may be desirable to have the reagent layer of lower permeability than is the spreading layer itself. This can readily be accomplished by reducing the effective pore size of the reagent layer. Relative permeability or porosity can be determined by well-known techniques.

Within the reagent layer is distributed an interactive mordant composition for bilirubin. The distribution of interactive composition can be obtained by dissolving or dispersing it in a matrix material, if used. Although uniform distributions are often preferred, they may not be necessary.

As is the case for a "wet chemistry" assay using an interactive mordant composition for bilirubin as described herein, one can also include in a "dry chemistry" analytical element of the invention an appropriate pH buffering composition. The buffering composition can be incorporated in the reagent layer or in one or more of the other layers present in a particular analytical element of the invention in an amount effective to impart to the reagent layer, under conditions of use of the element, a pH essentially identical to that employed in a "wet chemistry" assay as noted hereinabove.

In preparing integral analytical elements of this invention, the layers can be preformed as separate layers which are laminated together prior to use or maintained as separate layers until brought into fluid contact when the element is in use. Layers preformed as separate members, if coatable, are typically coated from solution or dispersion on a surface from which the layer can be physically stripped when dried. However, a convenient procedure which can avoid problems of multiple stripping and lamination steps when contiguous layers are desired, is to coat an initial layer on a stripping surface or a support, as desired, and thereafter to coat successive layers directly on those coated previously. Such coating can be accomplished by various well-known coating techniques as described in further detail in the aforementioned U.S. Pat. No. 3,992,158. Any interlayer adhesion problems can be overcome without harmful effect by means of surface treatments including extremely thin application of subbing materials such as are used in photographic films.

For coatable reagent layers, a coating solution or dispersion including the matrix material, if one is used, and interactive mordant compositions can be prepared, coated as discussed herein and dried to form a dimensionally stable layer. The thickness of any reagent layer and its degree of permeability are widely variable and depend on actual usage. Dry thicknesses of from about 10 microns to about 100 microns have been convenient, although more widely varying thicknesses may be preferable in certain circumstances. Fibrous reagent layers can be formed by impregnation of a fibrous matrix, in accordance with well-known techniques.

As mentioned previously herein, the present analytical elements can be self-supporting or carried on a support. Useful support materials include a variety of polymeric materials such as cellulose acetate, poly(ethylene terephthalate), polycarbonates and polyvinyl compounds such as polystyrenes, etc. A support of choice for any particular element will be compatible with the intended mode of result detection. Preferred supports include radiation-transmissive support materials that transmit electromagnetic radiation of a wavelength or wavelengths within the region between about 300 nm and about 700 nm. It may also be desirable to have a support that transmits one or more narrow wavelength bands and is opaque to adjacent wavelength bands. This could be accomplished, for example, by impregnating or coating the support with one or more colorants having suitable absorption characteristics.

In the layers of the element, it can be advantageous to incorporate one or more surfactant materials such as anionic and nonionic surfactant materials. They can, for example, enhance coatability of layer formulations and enhance the extent and rate of spreading in spreading layers that are not easily wetted by liquid samples in the absence of an aid such as a surfactant. In particular, it can be desirable to incorporate a relatively large amount of a surfactant, such as a non-ionic surfactant, in the spreading layer of the elements of the invention to normalize transport of bilirubin contained in an aqueous proteinaceous liquid sample in and through this layer of the element. Such normalization refers to obtaining within the spreading layer an equivalent penetration of the solvent medium and bilirubin contained in various applied samples of aqueous proteinaceous liquids, notwithstanding variations in protein concentration between such samples. In addition, it has been found that in the total bilirubin assay of the invention wherein bilirubin is often present in a "bound-state" such as bound to other proteins, e.g., serum albumin, the use of such surfactants in the spreading layer to achieve normalization of bilirubin transport advantageously appears to dissociate bilirubin bound to such protein. Preferred amounts of surfactant effective to achieve normalized bilirubin transport are typically between about 1% and about 15% by weight based on the dry weight of the layer. Further details regarding this use of surfactant materials to achieve normalized analyte transport may be found by reference to Goffe, Rand, and Wu, U.S. Pat. No. 4,050,898, issued Sept. 27, 1977.

Other optional interlayers may also be present in integral analytical elements employed as dry chemistry test elements used in the invention. For instance, a separate interlayer swellable in the solvent or dispersion medium of the liquid sample under analysis can be used. Such a swellable interlayer, preferably radiation-transmissive, e.g., a swellable gel layer, can be incorporated between the reagent layer and support of an integral analytical element and could be used to enhance the permeation or "spread rate" of a bilirubin-containing serum sample through the spreading layer into the reagent layer of the element. As another example an interlayer can be incorporated into an analytical element of the invention between the spreading layer and the reagent layer thereof. Such a layer should, of course, be permeable to bilirubin and can be used to incorporate reagent materials that can render various interferents for bilirubin inactive or can be used to filter and thereby remove such interferents. Or, in a further variation, such an interlayer can be used to incorporate a reagent that can be used to react with bilirubin. For example, a gelatin interlayer containing the enzyme glucuronidase can be employed between the spreading layer and the layer containing the interactive mordant composition whereby the enzymatic action of glucuronidase is used to convert conjugated bilirubin in the liquid sample under analysis into the unconjugated form of bilirubin. Alternatively, the enzyme glucuronidase may be incorporated in the spreading layer of an analytical element for more direct and efficient interaction of the enzyme on the bilirubin applied to the element.

As can be appreciated, dry chemistry analytical elements useful in the present invention can be configured in a variety of forms, including elongated tapes of any desired width, sheets or smaller chips.

Preferred dry chemistry analytical elements are used by applying to the element a sample of liquid under analysis. Typically, an element will be formed such that an applied sample will contact a spreading layer prior to the reagent layer and will first contact such spreading layer at its surface furthest removed from such reagent layer.

After sample application, and desirably after the liquid sample has been taken up by a spreading layer, the element is exposed to any conditioning, such as heating, humidification, or the like, that may be desirable to quicken or otherwise facilitate obtaining any test result. If an automated procedure is used, it can also be desirable to have any spreading layer accomplish its function within several seconds.

After the analytical result is obtained as a detectable change, it is measured, usually by passing the element through a zone in which suitable apparatus for reflection or transmission spectrofluorimetry is provided. Such apparatus would serve to direct a beam of energy, such as light, through the support and the reagent layer to excite the mordanted bilirubin in the reagent layer and stimulate fluorescent emission of light radiation by the mordanted bilirubin. This fluorescence emission would then be reflected, such as from an opacifying agent in the spreading layer of the element, back to a detecting means or would pass through the element to a detector, in the case of transmission detection. Various calibration techniques can be used to provide a control for the analysis. As one example, a sample of analyte standard solution can be applied adjacent to the area where the drop of sample is placed in order to permit the use of differential measurements in the analysis.

The following Examples are presented to further illustrate the practice of the invention.

In Examples 1-4, all fluorimetric determinations were obtained using a Turner Model 420 spectrofluorimeter (G. K. Turner Associates, Palo Alto, California) and a Perkin-Elmer 56 recorder (Perkin Elmer Corporation, Norwalk, Connecticut 06856). Wet assays, i.e., solution assays, as described in Examples 1-4, were conducted in a cylindrical quartz test tube having an inside diameter of about 1.0 cm.

Bilirubin employed in each of the Examples was obtained from bovine gallstones and was purchased from Sigma Chemical Co., St. Louis, Mo. Solutions of this bilirubin were prepared by solubilizing the crystalline bilirubin in distilled water after treating it with 0.1 N NaOH as described by Jacobsen, J. and Wennberg, R. P., "Determination of Unbound Bilirubin in the Serum of Newborns," *Clin. Chem.*, Vol. 20, p. 783-789 (1974).

The term "g/%" in the following examples refers to the amount of a substance in grams which is contained in 100 milliliters of liquid.

EXAMPLE 1

Fluorescence of Bilirubin in Absence and Presence of Interactive Mordant Composition (Wet Chemistry)

Fluorescence scans using 440 nm as the maximum excitation radiation wavelength (Ex) and 500 nm as the maximum emission wavelength (Em) were made of the following aqueous solutions:
 (a) bilirubin—1.9 mg/dl
 (b) Mordant 4 of Table I having an approximate molecular weight of about 500,000—0.042 g%
 (c) a mixture of (a) and (b) (same concentrations)

FIG. 1 shows that neither bilirubin nor Mordant 4 alone has any significant fluorescence in the 480–520 nm range when excited at 440 nm. However, when the two solutions are mixed together, there is generated a new emission peak at 502 nm.

It was noted that some fluorescent emission occurred in the 420 nm region with the mordant alone (possibly due to self-absorption of light by the polymer) which is of less intensity than the mixed peak and which disappears in the 500 nm region.

EXAMPLE 2

Dependence of Fluorescence on Mordant Concentration

Example 1 (c) was repeated except that the bilirubin concentration in the mixture was kept constant at 0.95 mg/dl while the concentration of Mordant 4 of Table I varied as shown in Table II. All mixtures were adjusted to a final volume of 2 ml. Fluorescence emission occurred similarly whether the aqueous medium used was distilled water or water buffered at pH 7.0 with 0.05 M sodium phosphate buffer.

Table II

| Final Conc. of Mordant 4 (g %) | Relative Fluorescence Intensity (%) |
|---|---|
| 0.010 | 39.8 |
| 0.017 | 53.9 |
| 0.027 | 59.3 |
| 0.032 | 67.0 |
| 0.034 | 61.9 |
| 0.042 | 70.5 |
| 0.051 | 83.3 |
| 0.059 | 82.5 |
| 0.085 | 100 |

As can be seen in Table II, the relative intensity of the fluorescence, which was observed immediately upon mixing with bilirubin, increased with increasing mordant concentration.

EXAMPLE 3

Dependence of Fluorescence on Bilirubin Concentration

Example 2 was repeated except that the mordant level was kept constant at 0.085 g%, and the bilirubin level varied as shown in Table III.

Table III

| Bilirubin (mg/dl) | Relative Fluorescence Intensity (%) |
|---|---|
| 0.048 | 51.6 |
| 0.095 | 76.0 |
| 0.29 | 94.9 |
| 0.48 | 96.5 |
| 0.71 | 100 |
| 0.95 | 98.1 |
| 1.19 | 77.2 |
| 1.43 | 63.3 |
| 1.67 | 59.2 |
| 1.9 | 47.5 |

As shown in Table III, at a constant mordant concentration (0.085 g%), the relative intensity of fluorescence increased with increasing bilirubin concentration up to about 0.7 mg/dl. Beyond this level, a decrease in fluorescence intensity was observed. This decrease in intensity is believed to be caused by a combination of factors including the filling of available binding sites on the mordant and by the progressive decrease in solubility of the mordant-bilirubin complex which occurs as the amount of bilirubin in the complex increases.

EXAMPLE 4

Alternative Bilirubin-Mordant Interactions

Example 1 tests were repeated using Mordants 1 and 6 of Table I at concentration levels of 0.095 g% and 0.085 g%, respectively. The approximate molecular weight of Mordant 1 was about 500,000 and that of Mordant 6 was about 1 billion. In the presence of 0.95 mg/dl of freshly prepared bilirubin, adequate fluorescence was observed although not as intense as that generated in Example 1. The wavelengths of fluorescence emission for Mordants 1 and 6 are shown in Table IV.

Table IV

| Mordant of Table I | $\lambda$max Ex | $\lambda$max Em |
|---|---|---|
| 1 | 440 | 500–502 |
| 6 | 440 | 495–500 |

EXAMPLE 5

Multilayer Analytical Element for the Fluorimetic Determination of Bilirubin (Dry Chemistry Test Element)

A multilayer element was prepared having a transparent poly(ethylene terephthalate) film support bearing, in order beginning with the layer closest to the support, a reagent layer containing polymeric Mordant 4 of Table I in an amount of 430 g/m$^2$; a poly(n-isopropylacrylamide) subbing layer and a spreading layer containing TiO$_2$ particles, blushed cellulose acetate and a surfactant. The spreading layer was prepared in a manner as described in Example 2 of Wu et al, U.S. Pat. No. 4,069,017.

Ten microliter samples of serum-based calibrator solutions having a pH of 7.3–8.0 and having varying levels of bilirubin (0–20 mg/dl range) were spotted onto the spreading layer of a series of identical multilayer elements having the structure described above and the elements were then incubated at 37° C. for 7 min. Fluorescence measurements were then obtained on the elements by reflection spectrophotometry from the mordant-containing layer through the transparent film support using 470 nm as the maximum excitation radiation (Ex), and 570 nm as the maximum emission radiation (Em). Results are shown in Table V.

Table V

| Bilirubin (mg/dl) | Relative Fluorescence Intensity (%) |
| --- | --- |
| 1.0 | 41.5 |
| 5.0 | 62.1 |
| 9.07 | 85.6 |
| 17.0 | 100 |

EXAMPLE 6

In this Example the fluorescence intensity of bilirubin, when mordanted by one of the preferred polymeric mordant compositions used in the present invention, was compared to that exhibited by bilirubin in the presence of certain other materials known to induce bilirubin fluorescence, namely, albumin and cetyltrimethyl ammonium bromide (CTAB). In this example, a series of identical 2.9 ml samples of bilirubin solution having a bilirubin concentration of 5.38 mg/dl was admixed with four different aqueous solutions and the fluorescence intensity exhibited by each of the resultant mixtures was compared. In each case, fluorescence intensity was measured using 440 nm wavelength light as the excitation radiation (Ex) and 520 nm wavelength light as the emission radiation (Em). The composition of each of the four different aqueous solutions tested and the fluorescence intensity exhibited by the final mixture of each of the different aqueous solutions with the 2.9 ml of bilirubin sample is shown in Table VI. As can be seen from the results of Table VI, the bilirubin mordanted by Mordant 4 of Table I exhibits a markedly higher fluorescence intensity than is produced by an identical amount of CTAB or an amount of albumin nearly three times greater than that of Mordant 4.

Table VI

| Fluorescence Inducing Agent Solution | Concentration of Fluorescence Inducing Agent In Mixture of Bilirubin Sample and Fluorescence Inducing Agent Solution | Percent Relative Fluorescence Exhibited by Mixture of Bilirubin Sample and Fluorescence Inducing Agent Solution |
| --- | --- | --- |
| 0.1 ml of aqueous solution of CTAB having a CTAB concentration of 615 mg/dl | 20.5 mg/dl* | 14 |
| 0.1 ml of aqueous solution of albumin having an albumin concentration of 1725 mg/dl | 57.5 mg/dl* | 20.6 |
| 0.1 ml of aqueous-methanol solution (3.33% by weight methanol) of Mordant 4 of Table I having a concentration of Mordant 4 of 615 mg/dl | 20.5 mg/dl | 100 |
| 0.1 ml of aqueous methanol mixture (3.33% by weight methanol) with no fluorescence inducing agent (control) | 0 | 0 |
| None (Control) | 0 | 0 (Relative fluorescence of bilirubin sample with no Fluorescence Inducing Agent Solution) |

*These concentrations of inducing agent were selected for comparative purposes as they are identical or similar to those used in the literature by J. Kresner and Cu et al in the aforementioned publications referenced in the "Summary of the Invention."

The invention has been described in detail with particular reference to certain preferred embodiments thereof, but it will be understood that variations and modifications can be effected within the spirit and scope of the invention.

We claim:

1. A fluorimetric method for the analysis of bilirubin in an aqueous liquid wherein said liquid and an interactive, polymeric mordant composition for bilirubin are contacted together to mordant bilirubin, said interactive, polymeric mordant composition having binding sites for bilirubin and comprising repeating units having a hydrophobic organic matrix and at least one charge-bearing cationic group, the novel step comprising subjecting the mordanted bilirubin to activating radiation effective to excite the mordanted bilirubin and produce detectable fluorescence indicative of the presence or concentration of bilirubin in said liquid.

2. A fluorimetric method for the analysis of bilirubin in an aqueous liquid which comprises
   (a) contacting together at a pH of from about 6.8 to about 9.5 said aqueous liquid and an interactive, polymeric mordant composition for bilirubin to mordant bilirubin, said interactive, polymeric mordant composition having binding sites for bilirubin and comprising repeating units having a hydrophobic organic matrix and at least one charge-bearing cationic group, (b) thereafter, or during step (a), subjecting the mordanted bilirubin to activating radiation effective to excite the mordanted bilirubin and produce detectable fluorescence; and (d) detecting said fluorescence to obtain a determination relating to the presence or concentration of bilirubin in said liquid.

3. The method of claim 2 wherein said interactive, polymeric mordant composition and said aqueous liquid are contacted together in a non-interfering liquid medium at a temperature of from about 15° to about 60° C.

4. The method of claim 2 wherein said aqueous liquid is a biological liquid.

5. The method of claim 2 wherein said aqueous liquid is serum.

6. The method of claim 2 wherein said aqueous liquid is serum which has been pretreated to reduce the amount of protein contained therein.

7. A fluorimetric method for the analysis of bilirubin in an aqueous liquid which comprises (a) contacting together said aqueous liquid and an interactive, polymeric mordant composition for bilirubin to mordant bilirubin, said interactive, polymeric mordant composition having binding sites for bilirubin and comprising repeating units having a hydrophobic organic matrix and at least one charge-bearing cationic group, said units having the formula

wherein A represents an organo group, Q represents a chemical bond(s) or a chemical group linking $M^{\oplus}$ to A, $M^{\oplus}$ represents a quaternary ammonium or phosphonium group, and $X^{\ominus}$ represents an acid anion;

(b) thereafter, or during step (a), subjecting the mordanted bilirubin to activating radiation effective to excite the mordanted bilirubin and produce detectable fluorescence; and (c) detecting said fluoresence to obtain a determination relating to the presence or concentration of bilirubin in said liquid.

8. A fluorimetric method for the analysis of bilirubin in an aqueous liquid which comprises (a) contacting together said aqueous liquid and an interactive, polymeric mordant composition for bilirubin to mordant bilirubin, said interactive, polymeric mordant composition having binding sites for bilirubin and comprising repeating units having a hydrophobic organic matrix and at least one charge-bearing cationic group, said units having the formula

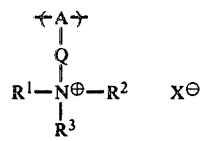

wherein A represents an organo group, Q represents a hydrocarbon group linking the nitrogen atom to A and contains from about 5 to 10 carbon atoms, each of $R^1$, $R^2$, and $R^3$, which may be the same or different, represents an alkyl having from 1 to about 10 carbon atoms or an aryl, aralkyl or alkaryl having from about 5 to 20 carbon atoms, and $X^{\ominus}$ represents an acid anion;

(b) thereafter, or during step (a), subjecting the mordanted bilirubin to activating radiation effective to excite the mordanted bilirubin and produce detectable fluorescence; and (c) detecting said fluorescence to obtain a determination relating to the presence or concentration of bilirubin in said liquid.

9. The method of claim 8 wherein said interactive, polymeric mordant composition for bilirubin is a copolymerized blend of monomers comprising (a) from about 25 to about 90 weight percent of monomer precursors for repeating units having the formula

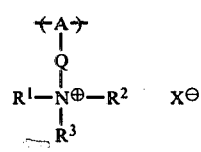

wherein A represents an alkylene group, Q represents a hydrocarbon group linking the nitrogen atom to A and contains from about 5 to 10 carbon atoms, each of $R^1$, $R^2$, and $R^3$, which may be the same or different, represents an alkyl having from about 4 to 10 carbon atoms or an aryl, aralkyl or alkaryl having from about 5 to 20 carbon atoms, and $X^{\ominus}$ represents an acid anion, (b) from about 10 to 75 weight percent of monomer precursors for non-interfering repeating units, said monomer precursors labelled (b) selected from the group consisting of aliphatic and aromatic hydrocarbons, alkyl acrylates, and alkyl methalcrylates, and (c) from 0 to about 5 weight percent of a difunctional crosslinking agent.

10. The method of claim 8 wherein said interactive, polymeric mordant composition is a material selected from the group consisting of poly(N,N,N-trimethyl-N-vinyl-benzylammonium) chloride; poly[styrene-co-benzyl(dimethyl)-p-vinyl-benzyl-ammonium chloride]; poly[styrene-co-N-vinylbenzyl-N-benzyl-N,N-dimethylammonium chloride-co-divinylbenzene]; poly(N,N,N-trimethyl-N-vinylbenzylammonium chloride-co-styrene); poly(N,N,N-trioctyl-N-vinylbenzylphosphonium chloride); and poly(styrene-co-(vinylbenzyl)-(trihexyl)-ammonium chloride).

11. A method as defined in claim 8 wherein said activating radiation comprises radiation having a wavelength within the range of about 420 to 475 nm and wherein said detectable fluorescence produced by said mordanted bilirubin is detected within the wavelength range of about 480 to 520 nm.

12. A fluorimetric method for the analysis of bilirubin in an aqueous liquid comprising (a) contacting together said aqueous liquid and an analytical element having an essentially dry reagent zone comprising an interactive, polymeric mordant composition for bilirubin to mordant bilirubin, said interactive, polymeric mordant composition having binding sites for bilirubin and comprising repeating units having a hydrophobic organic matrix and at least one charge-bearing cationic group, (b) thereafter, or during step (a), subjecting the mordanted bilirubin to activating radiation effective to excite the mordanted bilirubin and produce detectable fluorescence; and (c) detecting said fluorescence to obtain a determination relating to the presence of concentration of bilirubin in said liquid.

13. A fluorimetric method for the analysis of bilirubin in an aqueous liquid comprising (a) applying a sample of said aqueous liquid to a multi-zone element comprising a spreading zone and an essentially dry reagent zone, said spreading zone distributing and metering said sample to said reagent zone which contains an interactive, polymeric mordant composition for bilirubin to mordant bilirubin, said interactive, polymeric mordant composition having binding sites for bilirubin and comprising repeating units having a hydrophobic organic matrix and at least one charge-bearing cationic group, (b) thereafter, or during step (a), subjecting the mordanted bilirubin to activating radiation effective to excite the mordanted bilirubin and produce detectable fluorescence; and (c) detecting said fluorescence to obtain a determination relating to the presence or concentration of bilirubin in said liquid.

14. A fluorimetric method for the analysis of bilirubin in an aqueous liquid comprising (a) applying a sample of said aqueous liquid to an opaque, non-fibrous spreading layer of an integral multilayer element comprising a radiation transmissive support bearing, as superposed layers, an essentially dry reagent layer in fluid contact with an overlying layer representing said spreading layer, said spreading layer distributing and metering said liquid to said reagent layer which contains an interactive, polymeric mordant composition for bilirubin to mordant bilirubin, said interactive, polymeric mordant composition having binding sites for bilirubin and comprising repeating units having a hydrophobic organic matrix and at least one charge-bearing cationic group, (b) thereafter, or during step (a), directing activating radiation through said support to excite the mordanted bilirubin and produce detectable fluorescence, and (c) detecting said fluorescence through said support to obtain a determination relating to the presence or concentration of bilirubin in said liquid.

15. The method of claim 14 wherein said interactive, polymeric mordant composition for bilirubin is a polymer having repeating units of the following formula

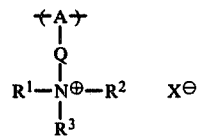

wherein A represents an organo group, Q represents a chemical bond(s) or a chemical group linking $M^{\oplus}$ to A, $M^{\oplus}$ represents a quaternary ammonium or phosphonium group, and $X^{\ominus}$ represents an acid anion.

16. The method of claim 14 wherein said interactive, polymeric mordant composition for bilirubin is a polymer having repeating units of the following formula:

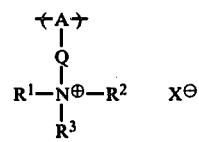

wherein A represents an alkylene group, Q represents a hydrocarbon group linking the nitrogen atom to A and contains from about 5 to 10 carbon atoms, each of $R^1$, $R^2$, and $R^3$, which may be the same or different, represents an alkyl having from 1 to about 10 carbon atoms or an aryl, aralkyl or alkaryl having from about 5 to 20 carbon atoms, and $X^{\ominus}$ represents an acid anion.

17. The method of claim 14 wherein said interactive, polymeric mordant composition for bilirubin is a copolymerized blend of monomers comprising (a) from about 25 to about 90 weight percent of monomer precursors for repeating units having the formula

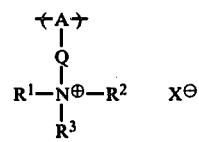

wherein A represents an alkylene group, Q represents a hydrocarbon group linking the nitrogen atom to A and contains from about 5 to 10 carbon atoms, each of $R^1$, $R^2$, and $R^3$, which may be the same or different, represents an alkyl having from about 4 to 10 carbon atoms or an aryl, aralkyl or alkaryl having from about 5 to 20 carbon atoms, and $X^{\ominus}$ represents an acid anion, (b) from about 10 to 75 weight percent of monomer precursors for non-interfering repeating units, said monomer precursors labelled (b) selected from the group consisting of aliphatic and aromatic hydrocarbons, alkyl acrylates, and alkyl methacrylates, and (c) from 0 to about 5 weight percent of a difunctional crosslinking agent.

18. The method of claim 14 wherein said interactive, polymeric mordant composition is a material selected from the group consisting of poly(N,N,N-trimethyl-N-vinyl-benzylammonium) chloride; poly[styrene-co-benzyl(dimethyl)-p-vinyl-benzyl-ammonium chloride]; poly[styrene-co-N-vinylbenzyl-N-benzyl-N,N-dimethylammonium chloride-co-divinylbenzene]; poly(N,N,N-trimethyl-N-vinylbenzylammonium chloride-co-styrene); poly(N,N,N-trioctyl-N-vinylbenzyl-phosphonium chloride); and poly(styrene-co-(vinylbenzyl)-(trihexyl)-ammonium chloride).

19. The method of claim 14 wherein said activating radiation comprises radiation having a wavelength within the range of about 420 to 475 nm and wherein said detectable fluorescence produced by said mordanted bilirubin is detected within the wavelength range of about 480 to 520 nm.

20. The method of claim 14 wherein said interactive, polymeric mordant composition is poly(styrene-co-(vinylbenzyl)-(trihexyl)-ammonium chloride).

* * * * *